United States Patent [19]
Saindon et al.

[11] Patent Number: 5,488,480
[45] Date of Patent: Jan. 30, 1996

[54] APPARATUS AND METHOD FOR DETECTING A HEAT SEAL IN A MOVING PLASTIC FILM

[75] Inventors: Stephen A. Saindon; Kevin O. Heindel, both of Appleton; James G. Morrow, Wauwatosa, all of Wis.

[73] Assignee: CMD Corporation, Appleton, Wis.

[21] Appl. No.: 197,216

[22] Filed: Feb. 16, 1994

[51] Int. Cl.⁶ ............... G01N 21/84; G01N 21/00
[52] U.S. Cl. ............... 356/429; 356/430; 356/237; 356/239; 250/559.4
[58] Field of Search ............... 356/429–431, 356/445, 448, 237, 239; 250/548, 557, 559.01, 559.04, 559.44; 226/45

[56] References Cited

U.S. PATENT DOCUMENTS

| | | | |
|---|---|---|---|
| 2,866,376 | 12/1958 | Cook | 356/430 |
| 3,125,265 | 3/1964 | Warren et al. | 356/431 |
| 3,206,606 | 9/1965 | Burgo et al. | 356/430 |
| 3,589,817 | 6/1971 | Sugaya | 356/430 |
| 3,992,111 | 11/1976 | Roulier et al. | 356/431 |
| 4,233,346 | 9/1980 | Neiheisel et al. | 356/430 |
| 4,431,309 | 2/1984 | Sick et al. | 356/431 |
| 4,642,084 | 2/1987 | Gietman, Jr. | 493/190 |
| 4,671,663 | 6/1987 | Sick | 356/431 |
| 4,934,993 | 6/1990 | Gietman, Jr. | 493/11 |
| 4,945,252 | 7/1990 | Lerner et al. | 250/548 |
| 4,972,088 | 11/1990 | Weyer et al. | 250/548 |
| 5,095,214 | 3/1992 | Eder | 356/431 |
| 5,184,190 | 2/1993 | Rai et al. | 356/239 |
| 5,260,766 | 11/1993 | Armitage | 356/239 |
| 5,301,129 | 4/1994 | McKaughan et al. | 356/429 |
| 5,386,293 | 1/1995 | Barnard et al. | 36/237 |

FOREIGN PATENT DOCUMENTS

| | | | |
|---|---|---|---|
| 56-101893 | 8/1981 | Japan | 356/237 |
| 62-163950 | 7/1987 | Japan | 356/237 |

*Primary Examiner*—Frank Gonzalez
*Assistant Examiner*—Jason D. Eisenberg
*Attorney, Agent, or Firm*—Foley & Lardner

[57] ABSTRACT

An apparatus and method are provided for detecting a formation or change in the consistency of a moving sheet material. The apparatus includes a radiation source, a radiation receiver, a support base for the sheet material, and a signal processor for producing a signal in response to the detection of a formation in the material. The apparatus may be modified to include moving or stationary support bases, and may be further modified to include structure for automatically positioning the source and receiver to optimize the detection of formations.

18 Claims, 1 Drawing Sheet

APPARATUS AND METHOD FOR DETECTING A HEAT SEAL IN A MOVING PLASTIC FILM

FIELD OF THE INVENTION

This invention relates to the detection of a seal or perforation in sheet material such as a plastic film. In particular, the present invention relates to the detection of a heat seal or perforation in a plastic film which is traveling at a high speed, where the film may be of the type used for making plastic bags.

BACKGROUND OF THE INVENTION

In equipment for handling sheet materials, such as plastic films in bag making machines, it is advantageous to provide registration indicators upon the material or film for purposes of sealing and perforating the film at selected locations. In particular, registration marks may be provided on film which allow the machine to seal or perforate the film with respect to the location of the registration mark. For example, in a bag making process, a perforation is provided in relation to a seal such that a continuous film including seals and perforations may be separated to provide individual bags. In the past, the perforation was mechanically registered to the seal such that the perforation was made in the proximity of the seal. While this arrangement provided satisfactory results, transient stretching in the film, film speed variations within a machine and operation of preceding process steps within the machine or in preceding machines resulted in distances between the seal and perforation which were not consistent. For example, the mechanical registration system may be set to provide a ¼ inch space between the seal and perforation, but due to film stretching, variations of film speed in the machine, or effects of preceding processes, the distance between the seal and perforation may vary within a range of ¼ inch, e.g., between ⅛ inch and ⅜ inch. In high speed machines, such variations can quickly cause unacceptable perforation to seal misregistration.

One known arrangement for detecting printed marks, such as registration marks, on web materials involves the use of a light source aligned generally perpendicular to the web and a sensor positioned substantially colinear with the light source. However, such an arrangement is not entirely successful at detecting features in certain sheet materials, and in particular, is not well suited to detecting a seal or perforation in plastic film materials.

Accordingly, it would be desirable to provide the capability to detect a seal in a plastic film and control film perforation such that perforations are directly registered with respect to the seal. However, in the past, it has been difficult to detect the presence of a seal in a moving film accurately and consistently. Thus, it would be desirable to provide a seal detection method and arrangement which can accurately and consistently detect a seal in a moving film, even where the film is moving at linear speeds in excess of 600 feet per minute. Additionally, it may be desirable to detect a perforation for properly separating bags being removed from a roll of bags and/or folded.

SUMMARY OF THE INVENTION

In accordance with a first aspect of the present invention, there is provided an apparatus for detecting a formation in a moving sheet material. The apparatus includes a support surface disposed on a first side of the material to support the moving sheet material, a radiation source disposed on the second side of the moving sheet material for emitting radiation towards the material, and a radiation receiver disposed on the second side of the material for receiving a portion of the radiation. The apparatus further includes a signal processor unit adapted to produce a signal representative of the intensity of the portion of the radiation.

In accordance with another aspect of the present invention, there is provided an arrangement for detecting a seal or perforation in a moving plastic film. The arrangement includes a support surface disposed to support a moving plastic film at an interface between the surface and the film, a first light guide positioned to direct a light to a location at the interface, a second light guide positioned to receive at least a portion of the light reflected away from the film, and an interface circuit coupled to the first and second light guides. The interface circuit produces a signal representative of an intensity of the light reflected and received.

In accordance with a further aspect of the present invention there is provided a method for detecting a formation in a moving sheet material. This method includes the steps of emitting radiation toward the moving sheet material, receiving at least a portion of the radiation reflected by the sheet material, and producing a signal in response to changes in this portion of radiation caused by the formation.

BRIEF DESCRIPTION OF THE DRAWINGS

An embodiment of the invention will hereinafter be described in conjunction with the drawings, wherein like designations denote like elements, and.

DETAILED DESCRIPTION OF THE PREFERRED EMBODIMENT

Figure 1:
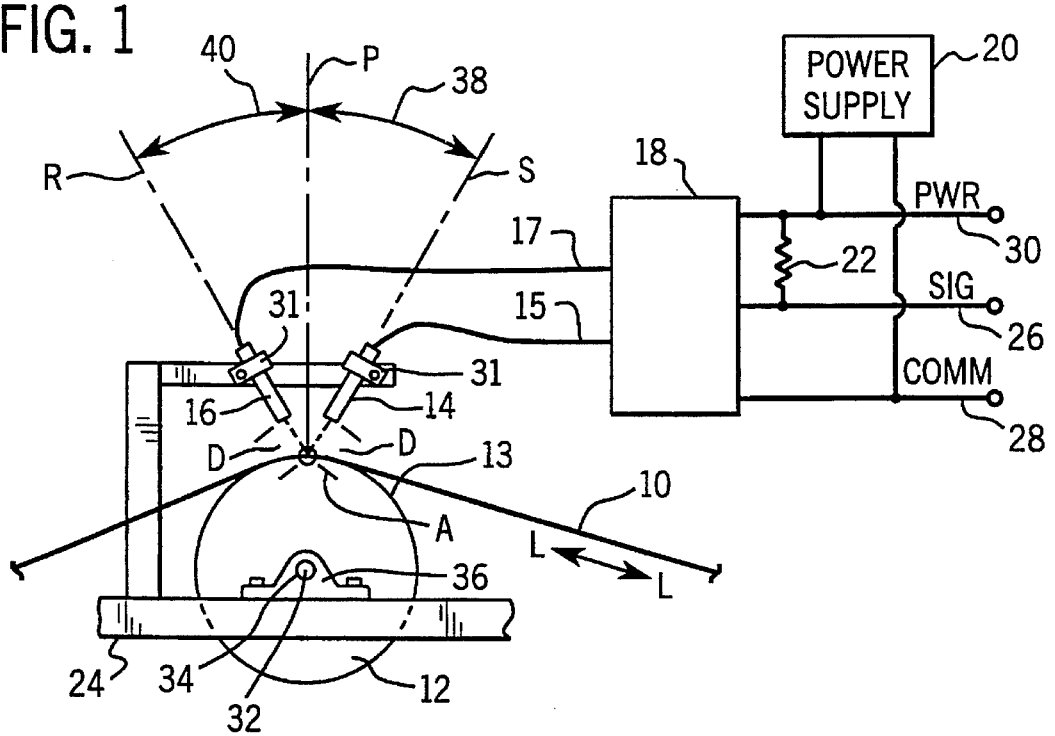
FIG. 1 illustrates an arrangement for detecting a seal or perforation in a moving film, where the arrangement includes a movable backing surface.

Referring to FIG. 1, there is illustrated an arrangement for detecting a desired formation (change in consistency) such as a heat seal or perforation in a moving film such as a plastic film 10. The arrangement includes a roller 12, a radiation source such as a fiberoptic sender 14, a radiation receiver such as a fiberoptic receiver 16, an interface unit 18, a power supply 20, a dropping resistor 22, and a support structure 24. The radiation source typically includes a light emitting diode (LED), while the receiver may include a photodiode of known type. These may be included in a single unit. By way of example only, sender 14 and receiver 16 unit may be of the type manufactured by MICROSWITCH having Part No. FE-T2A3, power supply 20 may be a 24 volt DC supply, resistor 22 may be a 2200 ohm carbon resistor, and structure 24 may be incorporated into the frame of a bag sealing and perforating machine arrangement (not shown). U.S. Pat. No. 4,642,084 and No. 4,934,993 issued to Peter J. Gietman on Feb. 10, 1987 and Jun. 19, 1990 describe machines for making plastic bags where the arrangement of the present invention may be incorporated. The disclosures of these patents are incorporated herein by reference. Interface unit 18 may include a number of elements manufactured by MICROSWITCH, including: a plug-in base, Part No. MPS33; a plug-in receptacle, Part No. MPB10; a control head, Part No. MPF6; and a multi-function timer/logic card, Part No. MPA133.

In general, radiation source or sender 14, receiver 16 and unit 18 interact such that when a seal, perforation, or registration mark passes a sensing position "A" below sender 14 and receiver 16, unit 18 drops the potential between signal line 26 and common line 28 from substantially 24 volts to substantially 0 volts. Additionally, upon detection of a seal, unit 18 also changes the potential between power line 30 and signal line 26 from substantially 0 volts to substantially 24 volts. In general, the detection of a seal, perforation, or registration mark results in the change in reflectance of the film and roller 12 below the seal. Either of these changes in voltage can be used as a formation (heat seal) detecting signal by a plastic film processing machine, such as a bag sealing and perforating machine, for the purpose of using this seal detection in various processes, such as selectively perforating a plastic seal in a predefined position with respect to a formation such as a seal.

Sender 14 and receiver 16 preferably each include a linear light wave guide arranged along a line substantially parallel to the heat seals in film 10. More specifically, in reference to FIG. 1, the heat seals in film 10 are substantially parallel with the longitudinal axis 32 of roller 12 and are perpendicular to the line of travel L—L of film 10 (see also FIG. 2). The linear light wave guide portions of sender 14 and receiver 16 are coupled to unit 18 via fiberoptic cables 15 and 17, respectively. Sender 14 provides a form of radiation such as infrared, visible green light or visible red light to the sensing position "A", where the light strikes the film and a portion of the light is reflected back to receiver 16. The type of light implemented may depend upon the type of film being processed. Additionally, the light source may be of continuous or pulsed light. Sender 14 and receiver 16 are fastened to support structure 24 with clamps 31.

Referring to FIG. 1, roller 12 has a substantially cylindrical shape having a width wider than the width of film 10. Roller 12 includes a shaft 34 which rotatably supports roller 12 between a pair of bearings 36 mounted to frame 24. Roller 12 may be a solid roller fabricated from aluminum and having a specially treated surface 13 to provide the proper light transmission between sender 14 and receiver 16. The transmission of light may include reflection from film 10 and surface 13. In particular, the surface may be a colored surface, preferably black, which is hardened and impregnated with teflon. This surface reduces friction between roller 12 and film 10, and also provides an effect upon light transmitted from sender 14 which enhances the ability of the arrangement to sense seals in film 10 (particularly more translucent and transparent films) moving at relatively high speeds (in excess of 600 linear feet per minute). By way of example, the roller surface may be treated with a Hard Lube impregnating process provided by Wisconsin Hard Coats of Milwaukee, Wis.

As discussed above, unit 18 includes a photoelectric sensor head and a signal interface module. The photoelectric sensor head provides the source of radiation, such as light, directed to sender 14 over fiber 15 and also includes an arrangement for monitoring the intensity of light received from receiver 16 via fiber 17. The signal interface module detects changes in the intensity of light provided to unit 18 by fiber 17. The signal interface module allows for the adjustment of sensitivity to changes in light intensity, changes in the duration of time for which the potentials between lines 30 and 26, and 26 and 28 are changed due to the detection of a seal, and allows for the adjustment of a time delay between the time a seal is sensed and the time the changes in potential between lines 26, 28 and 30 take place.

By way of example, unit 18 may include a timer logic card of the type manufactured by MICROSWITCH having Part No. MPA133. The timer logic card includes adjustments to provide the above-described ability to control the duration of potential changes between lines 26, 28 and 30 (pulse-width control), as well as the time delay for the purpose of delaying the point in time when unit 18 causes potential changes between lines 26, 28 and 30 due to the detection of a formation. The sensitivity of unit 18 to changes in the intensity of light provided by receiver 16 is controlled by the sensitivity adjustment on the control head.

Figure 2:
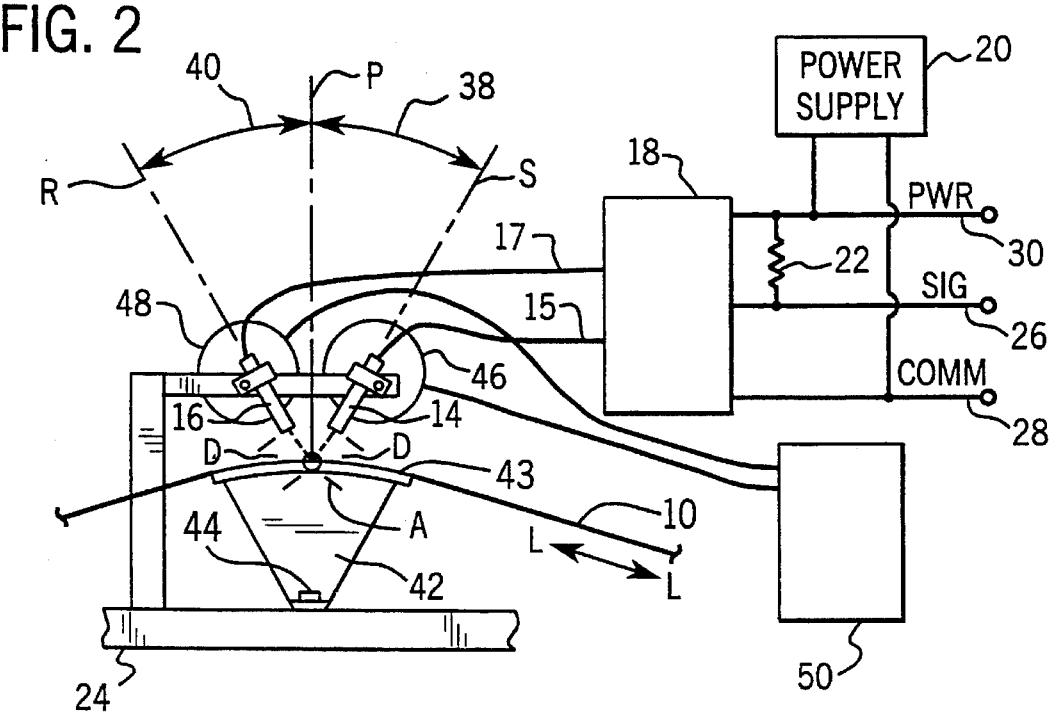
FIG. 2 illustrates an arrangement for detecting a seal or perforation in a moving film, where the arrangement includes a stationary backing surface.

Detecting a formation in a moving film 10 using sender 14 and receiver 16 depends upon the type of film and the underlying surface 13 supporting moving film 10 at the interface between film 10 and surface 13 (surface 43 in the FIG. 2 embodiment). More specifically, the light directed by sender 14 is directed along a plane "S" of sender 14 and strikes film 10 at the line where plane "S" intersects film 10 (position "A" at the interface). The characteristics of the combination of film 10 and underlying surface 13 affect the intensity of the light which is directed (reflected) back to receiver 16 along a plane "R" of receiver 16. Light affecting characteristics (e.g. reflection, absorption, and scattering properties) of film 10 and underlying surface 13 affect the intensity of the light which is received by receiver 16 and monitored by unit 18 for the purpose of providing a pulse via lines 26, 28 and 30.

To compensate for differences in light affecting characteristics of different films 10 in combination with surface 13, the orientation of the planes "S" and "R" of sender 14 and receiver 16 respectively are adjustable. More specifically, an angle 38 between plane "S" and a perpendicular plane "P", and an angle 40 between plane "R" and plane "P" are adjustable. Plane "P" is perpendicular to surface 13 at position "A". The adjustment of angles 38 and 40 has been performed based upon empirical data, and depends upon the type of surface 13 on roller 12 and color and type of film 10. Furthermore, without base surface 13, a consistent distance between sender 14, receiver 16 and film 10 is difficult to maintain, as are angles 38 and 40. Accordingly, without surface 13, it has been found that the detection of a formation such as a seal in moving film 10 can not be performed with sufficient consistency or accuracy to be useful for the purpose of seal detection in a high speed bag sealing and perforating machine. Additionally, properly selected, surface treatment for surface 13, such as a black Hard Lube coat, provides increased accuracy in detecting seals for a relatively large range of colors and types of film 10.

By way of example, the following Table A includes a list of materials where ranges for angles 38 and 40 have been determined based upon testing using infrared light. The materials tested were LLDPE (linear low density polyethylene), HDPE (high density polyethylene), and LDPE (low density polyethylene). This testing was conducted using a support structure 24 where the tips of sender 14 and receiver 16 were a distance D of approximately ⅜ of an inch from point "A".

TABLE A

| MATERIAL TYPE | RANGE OF ANGLE 38 | RANGE OF ANGLE 40 |
| --- | --- | --- |
| LLDPE - Clear | 13.5°–77.5° | 13.5°–77.5° |
| HDPE - Clear | 13.5°–77.5° | 13.5°–77.5° |
| LDPE - Black | 13.5°–77.5° | 13.5°–77.5° |
| LDPE - Orange | 13.5°–45° | 13.5°–45° |

By way of further example, the following Table B includes a list of materials where the sensitivity adjustment of the control head has been determined at various distances D, and angles 38 and 40. The values in Table B are turns of the adjustment screw in a MICROSWITCH control head model number MPF6.

TABLE B

| | Distance D (inches), Angles 38 & 40 (degrees) | | | | |
|---|---|---|---|---|---|
| MATERIAL | 11/32, 17° | 17/32, 13° | 9/16, 17° | 5/8, 45° | 3/4, 45° |
| LDPE - Orange | 5.5 | 1.5 | 3.5 | 4.5 | 4.5 |
| LDPE - Clear | 3.0 | 1.5 | 0.0 | 0.0 | 3.0 |
| LDPE - Black | 8.0 | 6.0 | 8.5 | 7.0 | 8.0 |
| HDPE - Clear | 1.0 | 1.5 | 0.0 | 0.0 | 0.0 |

Referring to FIG. 2, FIG. 2 illustrates a modified arrangement for sensing a formation such as a seal or perforation in moving film 10. The modification includes replacing roller 12 with a fixed support 42 over which film 10 may travel. Support 42 may be fabricated from aluminum to include an interface surface 43 which includes a Hard Lube treatment as does surface 13 of roller 12. Additionally, film 10 or surface 43 may be provided with lubricants to facilitate the sliding of film 10 relative to surface 43. Support 42 is fastened to support structure 24 with an appropriate fastener arrangement 44.

The embodiments of the arrangements described in reference to FIGS. 1 and 2 may be modified to include automatic positioning of sender 14 and receiver 16. More specifically, positioners such as stepping motors may be used to position sender 14 and receiver 16. In the preferred embodiment, sender 14 may be mounted upon the shaft of a stepping motor 46 and receiver 16 may be mounted upon the shaft of a stepping motor 48. Stepping motors 46 and 48 are controlled by a main control unit 50 which controls the device (bag sealing and perforating machine) utilizing the seal detection arrangement. By providing controller 50 with the type of film 10 for which seals are being detected, controller 50 may cause stepping motors 46 and 48 to rotate such that angles 38 and 40 are set to optimize the seal detection capability of the arrangement for a selected film 10. Of course, stepping motors 46 and 48 may include gear reductions to enhance the ability of the system to set angles 38 and 40.

Depending upon the application, stepping motors 46 and 48 may be replaced with other positioning arrangements such as linkages in combination with an air or hydraulic cylinder.

The preferred embodiment of the present invention has been disclosed by way of example and it will be understood that other modifications may occur to those skilled in the art without departing from the scope and spirit of the appended claims. For example, a preferred embodiment of the disclosed arrangement may be modified to detect formations or changes in the consistency of films other than plastic films.

What is claimed is:

1. An arrangement for detecting a heat seal in a film moving in a predetermined direction of travel comprising:

a support surface disposed to support the moving film at an interface between the surface and the film;

means, adjacent the interface, for directing radiation toward the interface along a line substantially parallel to a heat seal of interest and substantially perpendicular to the direction of travel, a portion of the radiation being reflected by the film at a varying intensity;

means, adjacent the interface, for receiving the portion of the radiation reflected by the film along the line;

means for producing a signal representative of the intensity of the portion of the radiation; and selectively adjustable means for monitoring the signal and for selectively detecting the heat seal in the moving film oriented substantially perpendicular to the direction of travel in response to changes in the intensity of the portion of the radiation.

2. The arrangement of claim 1, wherein the support surface includes the surface of a rotatable roller.

3. The arrangement of claim 1, wherein the support surface is stationary.

4. The arrangement of claim 1, wherein the means for directing and the means for receiving are light wave guides disposed at predetermined orientations with respect to the film.

5. The arrangement of claim 4, further comprising means for controllably adjusting the predetermined orientations.

6. The arrangement of claim 5, wherein the means for controllably adjusting comprises:

a first stepping motor disposed to support the means for directing and adjust its orientation;

a second stepping motor disposed to support the means for receiving and adjust its orientation; and means for controllably providing electrical power to the first and second stepping motors.

7. The arrangement of claim 1, wherein the means for producing and for selectively detecting comprises:

an infrared light source disposed to apply infrared light radiation to the means for directing; and a circuit disposed to receive the portion of the radiation, the signal being normally biased toward a first state and changing to a second state in response to the heat seal.

8. An arrangement for detecting a heat seal in a plastic film moving in a predetermined direction of travel comprising:

a support surface disposed to support the moving plastic film at an interface between the surface and the film;

a first light guide positioned to direct light toward the interface along a line substantially parallel to the heat seal in the film and substantially perpendicular to the direction of travel, a portion of the light being reflected by the film at varying intensity;

a second light guide positioned to receive the portion of the light reflected by the film along the line; and an interface circuit coupled to the first and second light guides, the interface circuit producing a signal representative of the intensity of the light reflected by the film, the interface circuit being adjustable for selectively detecting the heat seal in the film oriented substantially perpendicular to the path of travel based upon changes in the signal.

9. The arrangement of claim 8, wherein the support surface includes a rotatable roller surface.

10. The arrangement of claim 8, wherein the support surface is stationary.

11. The arrangement of claim 8, wherein the interface circuit comprises:

an infrared light source disposed to apply light in the form of infrared light to the first light guide; and a circuit disposed to receive the portion of the light reflected from the second light guide, where the signal is normally biased toward a first state and takes a second state in response to the seal.

12. The arrangement of claim 8, further comprising means for controllably adjusting orientations of the first and second light guides with respect to the film.

13. The arrangement of claim 12, wherein the means for controllably adjusting comprises:
- a first stepping motor disposed to support the first light guide and adjust its position;
- a second stepping motor disposed to support the second light guide and adjust its position; and
- means for controllably providing electrical power to the first and second stepping motors.

14. A method for detecting a heat seal in a plastic film moving in a predetermined direction of travel comprising the steps of:
 (a) supporting said moving film on a support surface;
 (b) emitting radiation toward said moving film on said support surface along a line substantially parallel to said seal and substantially perpendicular to the direction of travel to reflect a portion of said radiation from said film;
 (c) receiving said portion of said radiation reflected by said film along the line;
 (d) producing a first signal representative of said portion of said radiation; and
 (e) monitoring said first signal and selectively producing a second signal indicating detection of said seal in response to changes in said first signal.

15. The method as set forth in claim 14, further comprising the step of producing radiation.

16. The method as set forth in claim 14; wherein step (e) includes normally biasing said second signal toward a first state and altering said second signal to a second state in response to a change in said first signal caused by said seal.

17. The method as set forth in claim 14, wherein said radiation is emitted by an emitter having a first predetermined orientation with respect to said film and said portion of said radiation is received by a receiver having a second predetermined orientation with respect to said film, and wherein said method further comprises the step of selectively controlling said first and second orientations.

18. The method as set forth in claim 17, wherein said first and second orientations are selectively controlled by stepping motors in response to signals from a control unit.

* * * * *